United States Patent [19]
Bahler et al.

[11] 4,249,270
[45] Feb. 10, 1981

[54] ENDOPROSTHESIS FOR A KNEE JOINT

[75] Inventors: Andre Bahler; Norbert Gschwend; Heinrich Scheier, all of Zurich, Switzerland

[73] Assignee: Sulzer Brothers Limited, Winterthur, Switzerland

[21] Appl. No.: 80,671

[22] Filed: Oct. 1, 1979

[51] Int. Cl.³ ............................................... A61F 1/24
[52] U.S. Cl. .................................... 3/1.911; 128/92 C
[58] Field of Search ................................. 3/1.9–1.912, 3/22; 128/92 C

[56] References Cited
U.S. PATENT DOCUMENTS

| | | | |
|---|---|---|---|
| 3,795,922 | 3/1974 | Herbert et al. | 3/1.911 |
| 3,840,905 | 10/1974 | Deane | 3/1.911 |
| 3,868,730 | 3/1975 | Kaufer et al. | 3/1.911 |
| 4,094,017 | 6/1978 | Matthews et al. | 3/1.911 |

FOREIGN PATENT DOCUMENTS

| | | | |
|---|---|---|---|
| 2452412 | 5/1976 | Fed. Rep. of Germany | 3/1.911 |
| 2288509 | 5/1976 | France | 3/1.911 |
| 555671 | 11/1974 | Switzerland | 3/1.911 |

*Primary Examiner*—Ronald L. Frinks
*Attorney, Agent, or Firm*—Kenyon & Kenyon

[57] ABSTRACT

When the knee bends, the condyle-like bearing surfaces of the femur part of the prosthesis slide on the tibia-like rolling surfaces of the tibia part. The motion is guided by a web of the tibia part which engages in a fork-like mounting of the femur part. The web has a head which has a cylindrical shape to slide on a corresponding cylindrical section formed by a member mounted in the femur part. Web and mounting are preferably made of metal whereas the member in the femur part is made of another material, preferably, a moulded plastics member.

7 Claims, 5 Drawing Figures

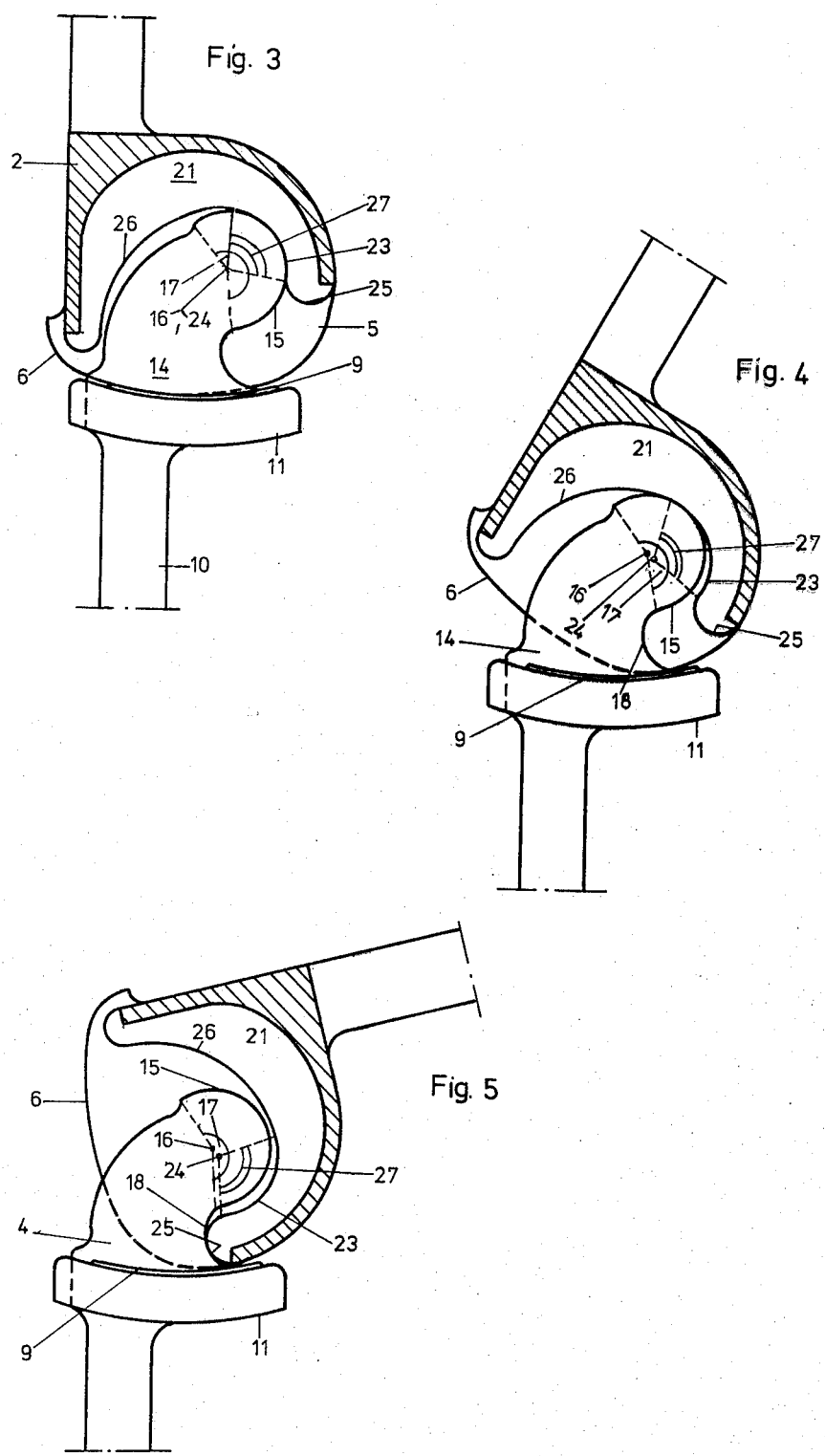

ENDOPROSTHESIS FOR A KNEE JOINT

This invention relates to an endoprosthesis for a knee joint.

Heretofore, it has been known to construct an endoprosthesis for a knee joint from a femur part and a tibia part. For example, the femur part has been provided with a stem via which the part can be secured in a femur and a fork-like mounting to define condyle-shaped bearing surfaces on opposite sides of a center plane of the part. The tibia part is, likewise, provided with a stem for anchoring in a tibia and includes a web which is engaged in the fork-like mounting and rolling surfaces on opposite sides of the web to cooperate with the bearing surfaces of the femur part. As described in Swiss Pat. No. 555,671, such a prosthesis can be provided with a moving guide shaft which is disposed in the fork-like mounting and which is guided in a slot in the web. The guide shaft is adapted, when the knee bends, to guide the femur part and the tibia part relative to one another so that the condyle-shaped bearing surfaces slide on the rolling surfaces of the tibia part in a substantially correct physiological manner.

In order to insure mechanical strength, both the web and the guide shaft are made of relatively rigid materials, and preferably one of the metals normally used for implants. In this known construction, the moving guide shaft does not have to bear or transmit any loads. However, it has been found in practice that considerable physiologically undesirable wear occurs between the web and the guide shaft.

Accordingly, it is an object of the invention to provide an endoprosthesis for a knee joint which includes a femur part and a tibia part but which eliminates a need for a guide shaft.

It is another object of the invention to avoid friction between the components of an endoprosthesis for a knee joint which are made of the same material.

It is another object of the invention to slidingly guide two parts of a knee joint endoprosthesis over one another during bending.

It is another object of the invention to maintain the tried basic features of a known endoprosthesis for a knee joint while providing a simple means for slidably guiding the components of the joint relative to each other.

Briefly, the invention provides an endoprosthesis for a knee joint which is comprised of a femur part having a fork-like end defining a pair of condyle-shaped bearing surfaces, means within the femur part to define a contoured boundary surface defining a curvilinear section and a following cylindrical section, and a tibia part having a pair of rolling surfaces, each disposed in opposition to a respective condyle-shaped bearing surface. In addition, the tibia part has a web of a material different from the boundary surface defining means which is disposed between the rolling surfaces and is curved in a direction away from the curvilinear section towards the cylindrical section of the boundary surface. The web also has a head with a peripheral surface of cylindrical shape.

When the femur part and tibia part are in a stretched position, the bearing and rolling surfaces are loaded and the centers of curvature of the cylindrical section of the boundary surface and head coincide with each other as well as with the axis of rotation of the knee joint. The shape and dimensions of the bearing and rolling surfaces and of the cylindrical section and head, including the centers of curvature, are adapted to each other such that, during bending of the parts from the stretched position, the bearing and rolling surfaces and the cylindrical section and head slide over one another.

The means which is disposed within the femur part to receive the head of the tibia part can be formed of a molded resilient plastics member which is secured, for example, adhesively within the femur part. In addition, the boundary surface of this member may further define a convex circular bead which follows the cylindrical section while the web of the tibia part defines a concave recess for receiving the bead upon bending of the parts from the stretched position over an angle of greater than 65° to 70°. Thus, during a bending of the knee joint through an angle of up to about 70°, the prosthesis parts are guided relative to one another by means of the cylindrical section and the cylindrical peripheral surface of the head. When bending exceeds 70°, guiding of the prosthesis parts is taken over by the bead and recess.

Advantageously, the web of the tibia part of the prosthesis is made from one of the metals normally used for implants whereas the member mounted in the femur part is made of a plastics such as HDPE or UHMW grade polyethylene which are normal endoprosthesis materials. Another advantage of this choice of materials is the substantial avoidance of convex guide surfaces of plastics which, as is know, cause considerable cold flow in the plastics ("The Scientific Basis of Joint Replacement", S. A. V. Swanson and M. A. F. Freeman, Pitman Medical Publishing Co. Ltd., Tunbridge Wells, Kent (1977), Page 61).

These and other objects and advantages of the invention will become more apparent from the following detailed description and appended claims taken in conjunction with the accompanying drawings in which:

FIG. 3 illustrates a view similar to FIG. 1 of the prosthesis parts in a stretched condition;

FIG. 4 illustrates a position of the prosthesis parts when bent through an angle of approximately 30° from the stretched position; and FIG. 5 illustrates a view of the prosthesis parts when bent through an angle of about 80° from the stretched position.

Figure 1:
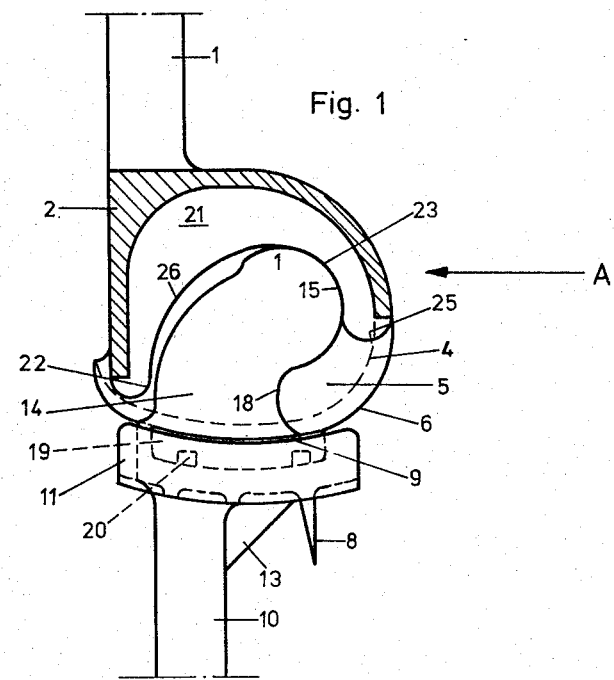
FIG. 1 illustrates a view taken on line I—I of FIG. 2 of a prosthesis according to the invention in a stretched position.

Referring to FIG. 1, the endoprosthesis for a knee joint is comprised of a top or femur part and a bottom or tibia part.

Figure 2:
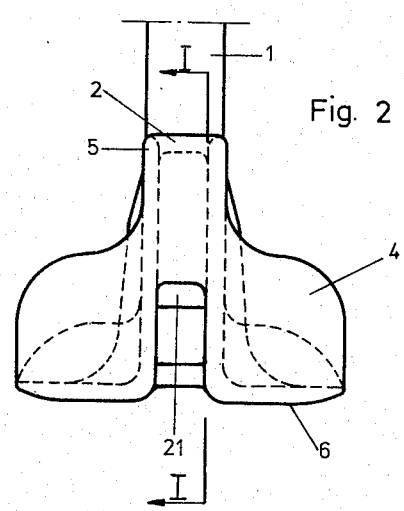
FIG. 2 illustrates the femur part of the prosthesis of FIG. 1 as viewed in the direction of arrow A of FIG. 1.

Referring to FIGS. 1 and 2, the femur part has a stem 1 which tapers towards the free end and is used for securing the part in a femur within a thigh. The stem 1 merges into a fork-like end or mounting 2 which defines a pair of plate-like limbs or sidewalls 5. Each limb is 5 is provided with a bearing projection 4 and a condyle-shaped bearing surface 6. As viewed in side elevation, the bearing surfaces 6 each form a curve made up of a number arcs having different radii and different centers of curvature. The shape and dimensions of the curve are purely empirical and substantially simulate the joint surfaces of a natural femur. The dimensions are, for example average values from a number of x-ray photographs of natural joints and are adjusted to insure that the femur part rolls on the tibia part in a substantially smooth manner.

The tibia part also has a stem 10 similar to the stem 1 of the femur part which is used to anchor the part in a tibia. In order to prevent accidental rotation of the tibia part, the stem 10 is secured by a triangular projection 13 and pins 8 which extend from the tibia part of the prosthesis into the tibia. As shown, the stem 10 merges into a bearing part 11 which has a pair of rolling surfaces 9 thereon, each of which is disposed in opposition to a respective condyle-shaped bearing surface 6 of the femur part. Each of the rolling surfaces 9 has a circular shape as view in side elevation. This circular shape is based on the surface of natural tibias. During bending and stretching of the prosthesis when in place, the bearing surfaces 6 can slide on the rolling surfaces 9.

The femur part and tibia part of the prosthesis are preferably made of a metal or metal alloy which is conventionally used for endoprostheses. Alternatively, the parts can be made, at least partly of bioceramics, pyrolytic carbon or another material of adequate strength which is of proved use for endoprostheses.

In order to prevent substantial friction between the metal parts which move relative to one another, plastic bodies 19 are secured on the tibia part to define the rolling surfaces 9. For example, the plastic bodies are made of polyethylene in order to form a low friction sliding surface. The bodies 19 may be secured in position by pins 20 and anchored by screws (not shown) in the bearing part 11. The plastic bodies 19 also provide some elasticity and shock-absorption between the two parts of the prosthesis, particularly when the parts are under load.

The tibia part also has a web 14 which is disposed between the rolling surfaces, i.e. between the plastic bodies 19 and has a rearwardly curved basic shape. The web 14 extends into the fork-like end 2 of the femur part between the limbs 5 and has a head thereon with a peripheral surface 15 of cylindrical shape. As indicated in FIG. 3, the cylindrical peripheral surface 15 of the head extends over an arc 17 of about 215° to 220°. The center of curvature 16 of this cylindrical surface 15 and the radius are determined experimentally. In addition, the center of curvature 16 is at least approximately on the axis of rotation of the joint when the prosthesis is stretched whereas the radius, relative to the other dimensions of the prosthesis, is chosen so as to insure an adequate guide surface on the cylindrical surface 15. The web 14 also defines a concave recess 18 at the dorsal end of the cylindrical peripheral surface 15. As shown, the recess 18 terminates at the point where the web 14 merges into the bearing part 11.

Referring to FIG. 1, the endoprosthesis also has a means within the femur part between the limbs 5 for forming a contoured boundary surface to receive the head of the web 14. This means is made of a material different from that of the web 14, for example, of a resilient molded plastics material, which is secured as by adhesion in the fork-like end 2 after being held in the correct position by pins (not shown). The boundary surface extends, when the knee joint is stretched, from the front bottom end, as viewed to the left in FIG. 1, approximately parallel to the shape of the web 14 in a first curvilinear section 26 as an arc upwards and backwards. The exact shape of the arc 26, which does not serve any special function, is unimportant provided the arc 26 prevents contact with the web 14 along the length of the arc, apart possibly from an abutment 22 at the front end for preventing excessive stretching of the knee since such contact will increase friction and possible wear. As shown, the curvilinear section 26 merges in to a following cylindrical section 23 after the arc 26 passes the apex of the boundary surface. In the example shown, the cylindrical section 23 extends over an arc 27 of about 105° (see FIG. 3). The radius of curvature of the section 23, apart from manufacturing tolerances, is equal to that of the cylindrical surface 15 of the head at the end of the web 14. The cylindrical section 23 also has a center of curvature 24 which, in the stretched position coincides with the center of curvature 16 of the surface 15 of the head. When the knee bends, the cylindrical section 23 forms a guide surface for the head of the web 14, i.e. for the tibia part of the prosthesis relative to the femur part.

As shown in FIG. 1, the web 14 is curved in a direction away from the initial curvilinear section 26 of the boundary surface towards the cylindrical section 23.

The boundary surface of the member 21 also defines a convex circular bead 25 which follows the cylindrical section 23. This bead 25 has a cylindrical surface which is of a smaller diameter than the cylindrical section 23 and is sized relative to the concave recess 18 of the web so as to be received therein upon bending of the prosthesis parts from the stretched position over an angle greater than 65° to 70° (see FIG. 5).

The position, dimension and position of the bearing surfaces 6 and rolling surfaces 9, the web 14, the head, the member 21 and cylindrical section 23 are adapted to one another so that static and dynamic forces are absorbed (completely in theory and substantially in practice) by the bearing surfaces 6 and rolling surfaces 9 as well as the head and cylindrical section 23 of the member 21 in conjunction with the aforementioned surfaces for guiding the bending motion of the knee.

Consequently, when the knee is stretched as shown in FIG. 3, the bearing surfaces 6 of the femur part rest on the rolling surfaces 9 of the tibia part. At this time, the centers of curvature 16, 24 coincide and the cylindrical surface 15 of the head and cylindrical section 23 of the member 21 abut one another. During bending up to an angle of about 70°, the bearing surfaces 6 slide on the rolling surfaces 9 while the head similarly slides on the cylindrical section 23 of the member 21. FIG. 4, shows the state corresponding to a joint bent through about 30°.

At an angle of 65° to 70°, the bead 25 at the rearend of the member 21 abuts the recess 18 of the web 14. Upon further bending, the bead 25 and recess 18 guide the two prosthesis parts as far as necessary. At the same time, the head and cylindrical section 23 of the member 21 move away from one another as shown in FIG. 5. In this regard, FIG. 5 shows a prosthesis joint to about 80°.

When the knee bends further, the bearing surfaces 6 and rolling surfaces 9 begin to move away from one another and the bead 25 slides upwards in the recess 18.

What is claimed is:
1. An endoprosthesis for a knee joint comprising
   a femur part having a fork-like end defining a pair of sidewalls, each said sidewall having a condyle-shaped bearing surface;
   a member mounted within said femur part between said sidewalls, said member having a contoured boundary surface defining a first curvilinear section and a following second cylindrical section having a center of curvature; and
   a tibia part having a pair of rolling surfaces each disposed in opposition to a respective condyle-shaped bearing surface and a web of a material different from said member between said rolling surfaces and extending into said fork-like end between said sidewalls, said web being curved in a direction away from said first curvlinear section towards said cylindrical section and having a head thereon with a peripheral surface of cylindrical shape, said peripheral surface having a center of curvature;

whereby, in a stretched position of said femur part and said tibia part, said bearing and rolling surfaces are loaded and said centers of curvature coincide with an axis of rotation of the knee joint and, during bending of said parts from said stretched position, said bearing and rolling surfaces and said cylindrical section and said head slide over one another.

2. An endoprosthesis as set forth in claim 1 wherein said boundary surface of said member further defines a convex circular bead following said cylindrical section and said web of said tibia part defines a concave recess for receiving said bead upon bending of said parts from said stretched postion over an angle of greater than 65% to 70%.

3. An endoprosthesis as set forth in claim 1 wherein said member is made of a molded resilient plastics material.

4. An endoprosthesis as set forth in claim 1 wherein each said part has a stem for anchoring in one of a femur and tibia, respectively.

5. An endoprosthesis for a knee joint comprising a femur part having a fork-like end defining a pair of condyle-shaped bearing surfaces;

means disposed within said femur part to define a contoured boundary surface defining a first curvilinear section and a following second cylindrical section having a center of curvature; and a tibia part having a pair of rolling surfaces each disposed in opposition to a respective condyle-shaped bearing surface and a web of material different from said means between said rolling surfaces, said web being curved in a direction away from said first curvilinear section towards said cylindrical section and having a head thereon with a peripheral surface of cylindrical shape, said peripheral surface having a center of curvature whereby, in a stretched position of said femur part and said tibia part, said bearing and rolling surfaces are loaded and said centers of curvature coincide with an axis of rotation of the knee joint and, during bending of said parts from said stretched position, said bearing and rolling surfaces and said cylindrical section and said head slide over one another.

6. An endoprosthesis as set forth in claim 5 wherein a pair of plastic bodies are secured on said tibia part to define said rolling surfaces.

7. An endoprosthesis as set forth in claim 6 wherein said means is a molded resilient plastics member secured to said femur part.

* * * * *

UNITED STATES PATENT AND TRADEMARK OFFICE
CERTIFICATE OF CORRECTION

PATENT NO. : 4,249,270

DATED : February 10, 1981

INVENTOR(S) : Andre Bahler, Et Al

It is certified that error appears in the above—identified patent and that said Letters Patent is hereby corrected as shown below:

Column 4, line 52, insert "bent" between "joint" and "to"

Signed and Sealed this

Twenty-sixth Day of May 1981

[SEAL]

Attest:

RENE D. TEGTMEYER

*Attesting Officer*     *Acting Commissioner of Patents and Trademarks*

UNITED STATES PATENT AND TRADEMARK OFFICE
CERTIFICATE OF CORRECTION

PATENT NO. : 4,249,270

DATED : February 10, 1981

INVENTOR(S) : Andre Bahler, et al.

It is certified that error appears in the above-identified patent and that said Letters Patent is hereby corrected as shown below:

In the front page, insert --Foreign Application Priority Data, Oct. 6, 1978 [CH] Switzerland ... 10392/78 --

Signed and Sealed this

Eleventh Day of June 1985

[SEAL]

Attest:

DONALD J. QUIGG

Attesting Officer    Acting Commissioner of Patents and Trademarks